US009056898B2

(12) United States Patent
Pekosz (10) Patent No.: US 9,056,898 B2
(45) Date of Patent: Jun. 16, 2015

(54) ATTENUATED RNA VIRUS AND APPLICATIONS THEREOF

(75) Inventor: Andrew Pekosz, Towson, MD (US)

(73) Assignee: Washington University, St. Louis, MO (US)

( * ) Notice: Subject to any disclaimer, the term of this patent is extended or adjusted under 35 U.S.C. 154(b) by 1134 days.

(21) Appl. No.: 12/235,011

(22) Filed: Sep. 22, 2008

(65) Prior Publication Data

US 2009/0142823 A1 Jun. 4, 2009

Related U.S. Application Data

(60) Provisional application No. 60/973,870, filed on Sep. 20, 2007.

(51) Int. Cl.

| | |
|---|---|
| *A61K 39/145* | (2006.01) |
| *A61K 39/12* | (2006.01) |
| *A61K 49/00* | (2006.01) |
| *C07K 14/005* | (2006.01) |
| *C12N 7/00* | (2006.01) |
| *A61K 39/00* | (2006.01) |

(52) U.S. Cl.
CPC ............. *C07K 14/005* (2013.01); *A61K 39/145* (2013.01); *A61K 2039/5254* (2013.01); *A61K 2039/5256* (2013.01); *C07K 2319/41* (2013.01); *C12N 7/00* (2013.01); *C12N 2760/00022* (2013.01); *C12N 2760/16122* (2013.01); *C12N 2760/16134* (2013.01); *C12N 2760/16162* (2013.01)

(58) Field of Classification Search
CPC ..... A61K 39/145; A61K 39/12; A61K 39/00; A61K 2039/6031; A61K 2039/6075; A61K 2039/70; A61K 38/00; A61K 2039/5256; A61K 2039/525; A61K 2039/5252; C07K 14/005; C07K 2319/00; C07K 16/1018; C07K 14/11; C07K 2319/42
See application file for complete search history.

(56) References Cited

U.S. PATENT DOCUMENTS 6,872,395 B2    3/2005  Kawaoka
2003/0194694 A1 * 10/2003 Kawaoka ...................... 435/5

FOREIGN PATENT DOCUMENTS

WO    WO 93/20196    * 10/1993

OTHER PUBLICATIONS

Iwatsuki-Horimoto et al., The Cytoplasmic Tail of the Influenza A Virus M2 Protein Plays a Role in Viral Assembly, 2006, Journal of Virology, vol. 80, No. 11, pp. 5233-5240.*
Chizhmakov et al. Selective proton permeability and pH regulation of the influenze virus M2 channel expressed in mouse erythroleukaemia cells, J. Physiol, 1996, pp. 329-336, vol. 494, Part 2.
Hoffman et al. A DNA transfection system for generation of influenza A virus from eight plasmids, PNAS, 2000, pp. 6108-6113, vol. 97, No. 11.
Holsinger et al. Influenza A Virus M2 Ion Channel Protein: a Structure-Function Analysis, J. Virol., 1994, pp. 1551-1563, vol. 68, No. 3.
Kaplan et al. In vitro synthesis of infectious poliovirus RNA, PNAS, 1985, pp. 8424-8428, vol. 82.
McCown et al, The Influenza A Virus M2 Cytoplasmic Tail is Required for Infectious Virus Production and Efficient Genome Packaging, J. Virol, 2005, pp. 3595-3605, vol. 79, No. 6.
Neumann et al. Generation of influenza A viruses entirely from cloned cDNAs, PNAS, 1999, pp. 9345-9350, vol. 96.
Racaniello et al, Cloned poliovirus complementary DNA is infectious in mammalian cells, Science, 1981, pp. 916-919, vol. 214, No. 4523.
Sakaguchi et al., The active oligomeric state of the minimalistic influenza virus M2 ion channel is a tetramer, PNAS, 1997, pp. 5000-5005, vol. 94.
Wu et al, Extending the Cytoplasmic Tail of the Influenza A Virus M2 Protein Leads to Reduced Virus Replication in Vivo but not in Vitro, J Virology, 2008, pp. 1059-1063, vol. 82, No. 2.
Watanabe et al, Novel Approach to the Development of Effective H5N1 Influenza A Virus Vaccines: Use of M2 Cytoplasmic Tail Mutants, J of Virology, 2008, pp. 2486-2492, vol. 82, No. 5.

* cited by examiner

*Primary Examiner* — Benjamin P Blumel
(74) *Attorney, Agent, or Firm* — Polsinelli PC (57) ABSTRACT

The invention encompasses an attenuated RNA virus and methods of using an attenuated RNA virus. The RNA virus comprises, in part, an ion channel protein comprising a peptide tag.

13 Claims, 5 Drawing Sheets

ATTENUATED RNA VIRUS AND APPLICATIONS THEREOF

CROSS REFERENCE TO RELATED APPLICATIONS

This application claims the priority of U.S. provisional application No. 60/973,870, filed Sep. 20, 2007, which is hereby incorporated by reference in its entirety.

GOVERNMENTAL RIGHTS

This invention was made with government support under grant number AI053629 and AI061252 awarded by the National Institutes of Health. The government has certain rights in the invention.

FIELD OF THE INVENTION

The invention encompasses an attenuated RNA virus, immunogenic compositions comprising an attenuated RNA virus, and methods of using an attenuated RNA virus.

BACKGROUND OF THE INVENTION

RNA viruses include viruses that cause HIV, the common cold, hepatitis, influenza, polio, mumps, measles, SARS, Ebola, and other diseases. Vaccination against RNA viruses is one way of protecting populations, both human and animal, from these diseases. In particular, vaccinating against influenza A virus is one means of controlling morbidity and mortality resulting from annual influenza epidemics.

Generally speaking, the immune response induced by a live, attenuated vaccine is believed to be superior to that induced by inactivated virus, resulting in increased protection against antigenic-drift variants and other antigenic subtypes. Live attenuated vaccines, however, potentially pose a greater risk to the host than an inactivated virus. In addition, methods used to attenuate the virus may affect the ability of the virus to induce a protective immune response in the host. Consequently, there is a need in the art for safe live attenuated vaccines that induce a protective immune response against an RNA virus in a host.

SUMMARY OF THE INVENTION

One aspect of the present invention encompasses an isolated RNA virus. The virus comprises an ion channel protein comprising a peptide tag.

Another aspect of the invention encompasses an immunogenic composition. The composition comprises at least one live attenuated RNA virus, the virus comprising an ion channel protein comprising a peptide tag.

Yet another aspect of the invention encompasses a method for inducing a protective immune response in a subject. The method comprises administering to the subject an immunogenic composition comprising at least one live attenuated RNA virus, the virus comprising an ion channel protein comprising a peptide tag.

Other aspects and iterations of the invention are described more thoroughly below.

BRIEF DESCRIPTION OF THE FIGURES

FIG. 1 illustrates the in vitro replication of recombinant influenza A viruses in MDCK cells. (A) presents a graph of the mean $TCID_{50}$ values and standard errors for the indicated virus at several time points. (B) is a plot of the diameters of 25 plaques for the indicated viruses. The solid horizontal line indicates the average plaque diameter.

FIG. 2 illustrates the in vivo replication and pathogenesis of recombinant influenza A viruses. Mice (n indicates the number of mice) were inoculated intranasally with the indicated viruses at the indicated doses. (A) presents a plot of survival over the course of two weeks. (B) B is a plot of body weight over the two weeks. Mouse weight was normalized to the weight at the time of infection and the average and standard error are graphed. At the indicated days post infection, viral loads were determined by $TCID_{50}$ in tracheas (C) and lungs (D). Each solid, horizontal line represents the average. The dashed, horizontal line indicates the limit of detection.

DETAILED DESCRIPTION OF THE INVENTION

In an attempt to differentially tag a virus, an antibody epitope tag was attached to the carboxyl terminal end of an ion channel protein of the virus. As expected, the addition of this tag did not alter the function of the ion channel protein or the in vitro replication of the virus. Unexpectedly, however, the addition of the tag attenuated the virulence of the virus, as judged by its inability to cause disease as compared to the parental strain of the virus. Furthermore, it was discovered that the attenuated virus comprising the peptide-tagged ion channel was able to provide protective immunity, indicating that it may be used as an immunogenic composition. This invention, therefore, encompasses the attenuated virus comprising a peptide-tagged ion channel protein, immunogenic compositions comprising the attenuated virus, and methods of using the compositions comprising the attenuated virus to provide protective immunity.

I. Isolated RNA Virus

One aspect of the present invention provides an isolated RNA virus comprising an ion channel protein comprising a peptide tag. Although the function of the peptide-tagged protein is not altered, the ability of the isolated RNA virus of the invention to induce disease is attenuated relative to that of a virulent strain of the same virus. Thus, the isolated RNA virus of the invention may be used to provide protective immunity.

(a) Types of Viruses

The parental strain of the isolated virus of the invention may be a wild type, a recombinant, or an attenuated virus. The attenuated virus may have at least one mutation that confers cold adaptation or altered growth, replication, and/or virulence. In general, the virus will be an RNA virus. For example, it may be a positive-sense single strand RNA virus, a negative-strand RNA virus, or a retrovirus. Non-limiting examples of suitable positive-strand RNA viruses include coronavirus, Dengue fever virus, hepatitis A, C, and E viruses, poliovirus, rhinovirus, Ross River virus, rubella virus, Sindbis virus, West Nile virus, and yellow fever virus. Non-limiting examples of suitable negative-strand RNA 
viruses include Ebola virus, hantavirus, human parainfluenza virus types 1-4, influenza A, B, and C viruses, Lassa virus, Marburg virus, measles virus, mumps virus, Nipah virus, respiratory syncytial virus, rabies virus, and rinderpest virus. Suitable examples of retroviruses include human immumo-deficiency virus, human T-lymphotropic virus, and feline immunodeficiency virus. Exemplary viruses include influenza A, B, and C viruses, coronavirus, hepatitis C virus, and human immunodeficiency virus. An especially preferred virus is an influenza A virus. Influenza A virus may be further subdivided into subtypes on the basis of the two main sur may be a Vpu protein and/or Vpr protein. In another embodiment, the isolated RNA virus may be a hepatitis C virus and the ion channel protein may be a p7 protein. In still another embodiment, the isolated RNA virus may be a coronavirus and the ion channel protein may be an E protein. In another alternate embodiment, the isolated RNA virus may be an influenza C virus and the ion channel protein may be a CM2 protein. In yet another embodiment, the isolated RNA virus may be an influenza B virus and the ion channel protein may be a BM2 protein. In a preferred embodiment, the isolated RNA virus may be an influenza A virus and the ion channel protein may be an M2 protein. In another preferred embodiment, the isolated RNA virus may be an influenza A virus, the ion channel protein may be an M2 protein, and the peptide tag may be at the carboxyl terminus of the protein. In an especially preferred embodiment, the isolated RNA virus may be an influenza A virus, the ion channel protein may be an M2 protein, and the carboxyl terminal peptide tag may be the myc antibody epitope tag.

(c) Properties of the Isolated RNA Virus

In general, the function of the peptide-tagged ion channel protein is similar to that of the native (untagged) ion channel protein. The ion channel activity of the protein may be measured using techniques known to those of skill in the art. For example, ion channel activity may be measured directly in mammalian cells (e.g., Chizhmakov et al. (1996) J. Physiol. 494(Pt. 2):329-336), indirectly in *Xenopus* oocytes (e.g., Holsinger et al. (1994) J. Virol. 68:1551-1563), or indirectly via the fowl plague virus (FPV) HA protein rescue assay (e.g., McCown and Pekosz (2005) J. Virol. 79(6):2595-3605). Each of the afore mentioned articles is incorporated by reference in its entirety.

The in vitro replication of the isolated RNA virus of the invention is generally similar to that of a wild type strain of the same species of virus. Viruses may be grown in a number of primary cells, including monkey kidney, calf kidney, hamster kidney and chicken kidney. Viruses may also be grown in continuous cell lines, including Madin-Darby canine kidney (MDCK) cells, 293T human embryonic kidney cells, African green monkey kidney epithelial (Vero) cells, Madin-Darby bovine kidney (MDBK) cells, baby hamster kidney (BHK) cells, North African green monkey kidney fibroblast (CV-1) cells, Chinese hamster ovary (CHO) cells, TM4 mouse Sertoli cells, HeLa human cervical epitheloid carcinoma cells, buffalo rat liver (BRL) cells, WI-38 human diploid lung cells, Hep G2 human hepatocellular carcinoma cells, and mouse mammary tumor (MMT) cells. The optimal culture conditions (i.e., media, supplements, temperature, $CO_2$ concentration, etc.) for a particular type of cell, as well as means to infect cells with the particular virus are known to those skilled in the art.

Virus replication may be determined by a variety of techniques that are known to those skilled in the art. For example, the viral titer may be determined using a tissue culture infectious dose$_{50}$ (TCID$_{50}$) assay or a plaque forming unit (pfu) assay. A TCID$_{50}$ unit is the amount of a virus that results in a cytopathic effect in 50% of the infected cells. Virus replication may also be monitored with a plaque assay in which the number and/or diameter of plaques are quantified and/or the morphology of the plaques is denoted. Still another method that may be used to monitor virus replication is a hemagglutination assay. Alternatively, virus replication may be determined by directly counting the number of viral particles using an electron microscope. Additionally, virus replication may also be monitored with a PCR assay, an antibody based assay, or a branched DNA assay.

The in vivo replication of the isolated RNA virus of the invention is generally reduced relative to that of a wild type strain of the same species of RNA virus. In some embodiments, the in vivo replication is reduced by about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0 logs, or more, relative to that of a wild type strain. A virus may be administered to a subject by a variety of means, including, but not limited to, transmucosally (e.g. orally, nasally, ocularly, or rectally), transdermally, parenterally (e.g., via intravenous injection, as well as, intra-arteriole, intramuscular, intradermal, subcutaneous, intraperitoneal, intraventricular, and intracranial), or topically. The replication of the virus in the subject may be determined by the same techniques mentioned above for in vitro replication. Depending upon the type of virus, the viral load may be determined in a body fluid (e.g., blood, serum, saliva, cerebrospinal fluid, pleural fluid, lymphatic fluid, milk, sputum, semen, and urine), a cell, a cell extract, or a tissue sample. The body fluid, cells, or tissue sample may be obtained by biopsy or surgery. Those of skill in the art will appreciate that the type of body fluid or tissue analyzed will depend upon the particular type of virus. For example, replication of influenza A virus may be monitored in cells and/or fluid from the lungs or trachea.

Advantageously, the ability of the isolated RNA virus of the invention to cause disease is attenuated relative to that of a wild type strain of the same virus. The isolated RNA virus of the invention, therefore, is an attenuated, less virulent virus. Preferably, viral virulence may be monitored in an appropriate animal model of infection. The pathogenicity or virulence of a virus may be measured via a variety of means. For example, the morbidity of the viral disease may be assessed by monitoring weight loss, changes in body temperature, fluid loss, and/or protein or enzyme levels. The mortality of the viral disease may be assessed by monitoring survival and/or death. Those of skill in the art will know the appropriate test or measurement to use to assess the virulence of the particular virus.

Furthermore, the isolated RNA virus of the invention generally elicits an immune response in the subject. The immune response may be a humoral response (i.e., mediated via B cells) and/or a cell mediated response (i.e., mediated via T cells). The cell mediated response may be a cytotoxic T lymphocyte (CTL) and/or a delayed type hypersensitivity (DTH) response. Techniques to assess immune responses are well known in the art (e.g., see Harlow and Lane (1988) "Antibodies. A Laboratory Manual," Cold Spring Harbor Laboratory Press, Cold Spring Harbor, N.Y.). In exemplary embodiments, the induced immune response generally protects the subject against challenge with a virulent stain of the same species of virus. Thus, the isolated RNA virus of the invention may be used to protect a subject from disease caused by a virulent species, strain, or sub-type of the virus.

II. Immunogenic Composition

Another aspect of the present invention provides an immunogenic composition comprising at least one live attenuated RNA virus of the invention, as described above in section I. Administration of an immunogenic composition of the invention to a subject typically does not induce disease, but rather elicits a humoral and/or cellular immune response and protects the subject from challenge against a virulent strain of the same or a closely related virus.

To make an immunogenic composition, the attenuated RNA virus of the invention will generally be produced in host cells that have been approved and certified according to the WHO requirements for vaccine production (Mizrahi, ed., Viral Vaccines, Wiley-Liss Inc., NY, pp. 39 60, 1990). WHO certified, or certifiable, continuous cell lines are preferred for producing the immunogenic composition. The requirements for certifying such cell lines include characterization with respect to at least one of genealogy, growth characteristics, immunological markers, virus susceptibility, tumorigenicity, and storage conditions, as well as by testing in animals, eggs, and cell culture. Such characterization is used to confirm that the continuous cell lines are free from detectable adventitious agents. In some countries, karyology may also be required. In addition, tumorigenicity is preferably tested in cells that are at the same passage level as those used for vaccine production. Suitable host cells include embryonated hens' eggs, Vero cells, or other mammalian cells. Non-limiting examples of cell lines that may be suitable include, but are not limited to, mammalian fibroblast or epithelial cells maintained as continuous cell lines. Further non-limiting examples include Vero, MDCK, 293T, BK-21 and CV-1 cells, readily available from commercial sources (e.g., ATCC, Rockville, Md.).

In some embodiments, an attenuated RNA virus of an immunogenic composition may have at least one additional attenuating mutation, in addition to the peptide-tagged ion channel protein. The additional mutation may be in a gene that affects cold adaptation, replication, growth control, or virulence. For example, in one embodiment, the attenuated RNA virus of an immunogenic composition may be an influenza A virus comprising a peptide-tagged M2 protein, as well as a deletion in the NS1 coding region. In another embodiment, the attenuated RNA virus of an immunogenic composition may be an influenza A virus comprising a peptide-tagged M2 protein, as well as an altered HA cleavage site. In still another embodiment, the attenuated RNA virus of an immunogenic composition may be an influenza A virus comprising a peptide-tagged M2 protein, as well as an altered temperature sensitivity.

In other embodiments, at least one gene that encodes an antigenic viral protein of interest may be introduced into the attenuated RNA virus of the invention comprising an immunogenic composition. For example, genes encoding HA and/or NA proteins of influenza A may be introduced into an attenuated influenza A virus comprising a peptide tagged M2 protein.

In alternate embodiments, an immunogenic composition may further comprise at least one additional live attenuated virus (i.e., in addition to the attenuated virus of the invention). The additional attenuated virus may harbor temperature-sensitive mutations that limit its growth in the natural host. Furthermore, the additional attenuated virus may have mutations in genes that reduce its replication or mutations in virulence genes that reduce its virulence. In another embodiment, an immunogenic composition may further comprise at least one inactivated virus. The inactivated virus may be killed by heat or chemical (formaldehyde) treatment. An inactivated virus is, therefore, unable to replicate, but maintains its antigenic constitution and immunogenicity. In yet another embodiment, an immunogenic composition may further comprise a purified viral protein, such as a viral coat protein, a surface glycoprotein, etc.

In a preferred embodiment, an immunogenic composition may comprise at least one live attenuated influenza A virus carrying a carboxyl terminal tagged M2 protein. The influenza A virus may be an H1N1 subtype, an H1N2 subtype, an H3N2 subtype, an H5N1 subtype, or a combination thereof. In another preferred embodiment, an immunogenic composition may comprise an H1N1 subtype of an influenza A virus, an H3N2 subtype of an influenza A virus, and an influenza B virus. In still another preferred embodiment, an immunogenic composition may comprise an influenza A virus and an influenza B virus.

An immunogenic composition of the invention may further comprise one or more adjuvants, carriers, and/or excipients. Adjuvants are typically substances that generally enhance the immune response of a subject to a specific antigen. Suitable adjuvants include, but are not limited to, complete Freund's adjuvant, incomplete Freund's adjuvant, other bacterial cell wall components, aluminum-based salts, calcium-based salts, silica, polynucleotides, toxoids, serum proteins, viral coat proteins, other bacterial-derived preparations, gamma interferon, block copolymer adjuvants, such as Hunter's Titermax adjuvant (available from CytRx Corp. Inc., Norcross, Ga.), Ribi adjuvants (available from Ribi ImmunoChem Research, Inc., Hamilton, Mo.), and saponins and their derivatives, such as Quil A (available from Superfos Biosector A/S, Denmark). Carriers are typically compounds that increase the half-life of a therapeutic composition in a treated subject. Suitable carriers include, but are not limited to, polymeric controlled release formulations, biodegradable implants, liposomes, oils, esters, and glycols. An excipient is generally an inert substance used as a diluent or a vehicle for delivery. Examples of suitable excipients include water, saline, Ringer's solution, dextrose solution, Hank's solution, and other aqueous physiologically balanced salt solutions. Other useful formulations include suspensions containing viscosity enhancing agents, such as sodium carboxymethylcellulose, sorbitol, or dextran. Excipients may also contain minor amounts of additives, such as substances that enhance isotonicity and chemical stability. Examples of buffers include phosphate buffer, bicarbonate buffer, and Tris buffer, while examples of preservatives include thimerosal, m- or o-cresol, formalin and benzyl alcohol. Preferably, the adjuvant, carrier, and/or excipient are pharmaceutically acceptable.

The term "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

III. Method for Providing Protective Immunity

A further aspect of the invention encompasses a method for providing protective immunity to a subject by administering an immunogenic composition comprising at least one live attenuated RNA virus comprising a peptide tagged ion channel protein. Immunogenic compositions were described above in section II and the attenuated RNA virus was described above in section I.

An immunogenic composition of the invention may be administered to a subject by a variety of means. Suitable means include, but are not limited to, transmucosal administration (e.g., oral, intranasal, intraocular, or rectal), transdermal administration, parenteral administration (e.g., via intravenous injection, as well as, intra-arteriole, intramuscular, intradermal, subcutaneous, intraperitoneal, intraventricular, and intracranial injection), or topical administration. For example, in embodiments in which the attenuated virus of an immunogenic composition is an influenza virus, a preferred method to administer the immunogenic composition is by intranasal administration. Such administration may be accomplished by use of a syringe fitted with cannula, or by use of a nebulizer fitted over the nose and mouth of the subject.

The dose of an immunogenic composition administered to a subject can and will vary, depending upon a variety of factors. In general, an immunogenic composition will comprise an amount of live attenuated RNA virus of the invention that is sufficient to protect the subject, for a suitable period of time, from challenge with a virulent strain of the virus. The amount of live attenuated RNA virus may range from about $10^3$ TCID$_{50}$ units of virus to about $10^8$ TCID$_{50}$ units of virus, or more preferably from about $10^5$ TCID$_{50}$ units of virus to about $10^7$ TCID$_{50}$ units of virus.

The number of doses and/or frequency of dose administration can and will vary. In one embodiment, the subject may be protected from challenge with a virulent species of the virus by administering a single dose of an immunogenic composition of the invention. A suitable single dose is a dose that is capable of protecting the subject from challenge with a virulent species of the virus when administered one time. In another embodiment, multiple doses may be administered over a period of time that ranges from about two weeks to about two years. In still another embodiment, a booster dose may be administered at some interval of time after the original administration. Booster administrations preferably are administered when the immune response of the subject becomes insufficient to protect the subject from from challenge with a virulent strain of the virus.

The efficacy of an immunogenic composition of the invention to generate an immune response may be tested in a variety of ways. Humoral immunity may be assessed by a variety of methods, including the detection of antibodies via an immunoassay, such as an ELISA assay, a Western blot, a dot blot, a radioimmune assay, a qualitative immunoassay, or a colorimetric assay, or a hemagglutination inhibition (HAI) test. Furthermore, if the immunogenic composition comprises an attenuated RNA virus comprising an antibody epitope tagged ion channel protein, then an immunized subject may be differentiated from an infected subject. An immunized subject may generate antibodies against the epitope tag, as well as antibodies against viral proteins or other antigens. Additionally, cellular immunity may be monitored by the detection and/or analysis of a population of activated T cells (e.g., via the detection of specific cytokines synthesized and secreted by the activated cells). For example, a specific cytokine may be detected via an ELISA assay, fluorescent activated flow cytometry, or an immunofluorescent microscopy assay.

An immunogenic composition of the invention may be administered to a variety of subjects. In general, the subject will be a human or an animal that is susceptible to the disease caused by the RNA virus of interest. The subject may be a mammal, such as a human, a companion animal, such as cat or a dog, an agricultural animal, such as dairy cattle, beef cattle, a goat, a sheep, a swine, a horse, or another equid, a zoo animal, such as a primate, a lion, a mink, etc., a laboratory animal, such as a mouse, rat, or hamster, or a marine mammal, such as a whale or a seal. The subject may also be a domestic fowl, such as a chicken, goose, or duck, a game fowl, or an aquatic bird. In an exemplary embodiment, the subject may be a human. While the age and the general health status of the subject may vary, the subject is generally not immunocompromised.

In general, administration of an immunogenic composition comprising an attenuated RNA virus comprising a peptide tagged ion channel protein induces an immune response, provides protective immunity, and prevents disease caused by a virulent strain of the virus.

As various changes could be made in the above compositions and methods without departing from the scope of the invention, it is intended that all matter contained in the above description shall be interpreted as illustrative and not in a limiting sense.

DEFINITIONS

To facilitate understanding of the invention, a number of terms are defined below.

The term, "attenuated," as used here, refers to a virus that is capable of stimulating an immune response and creating immunity but not causing illness.

As used herein, the term, "peptide tag," refers to an exogenous amino acid sequence that is added to a protein.

As used herein, the phrase "protective immune response," or "protective immunity," refers to an immune response in a host that protects the host from challenge with a virus of the same species. A host is "protected from challenge" when the immune response contributes to the lessening of any symptoms associated with infection of a host with the virus. For example, a protective immune response against influenza will induce an immune response that helps to ameliorate symptoms associated with influenza infection or reduces the morbidity and mortality associated with influenza infection. The use of the term "protective" in this invention does not necessarily require that the host is completely protected from the effects of the virus.

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

The following examples illustrate various embodiments of the invention.

Example 1

Epitope Tagging of the M2 Protein and in vitro Virus Replication

In order to further characterize the role of the M2 cytoplasmic tail in the influenza A life cycle, a recombinant influenza A virus was generated in which the myc epitope tag was attached to the carboxyl terminus of the M2 protein. The addition of an antibody epitope tag to the M2 protein cytoplasmic tail does not alter the ion channel activity or expression of the protein (Sakaguchi et al., (1997) Proc. Natl. Acad. Sci. USA 94:5000-5005).

The recombinant influenza A/WSN/33 virus that contained the myc-epitope (rWSN M2myc) was generated using standard procedures. Briefly, the nucleotide sequence (5'-GAG-CAGAAGCTGATCTCCGAGGAAGACCTG-3', SEQ ID NO:18) of the myc epitope tag (amino acids, EQKLISEEDL, SEQ ID NO:1) was introduced in place of the M2 stop codon in the vector pHH21 M segment. This plasmid encodes the M segment of the A/WSN/33 strain of influenza A virus, see McCown and Pekosz (2005) and Neumann et al. (1999). The recombinant virus encoding this sequence was recovered via standard methodology, as described by McCown and Pekosz (2005) and Neumann et al. (1999). The presence of the myc epitope nucleotide sequences was verified by reverse transcriptase polymerase chain reaction followed by DNA sequencing. The presence of the myc epitope in the M2 protein was verified by Western blotting of virus-infected cell lysates with antibodies that recognize the M2 protein or the myc epitope.

Figure 1:
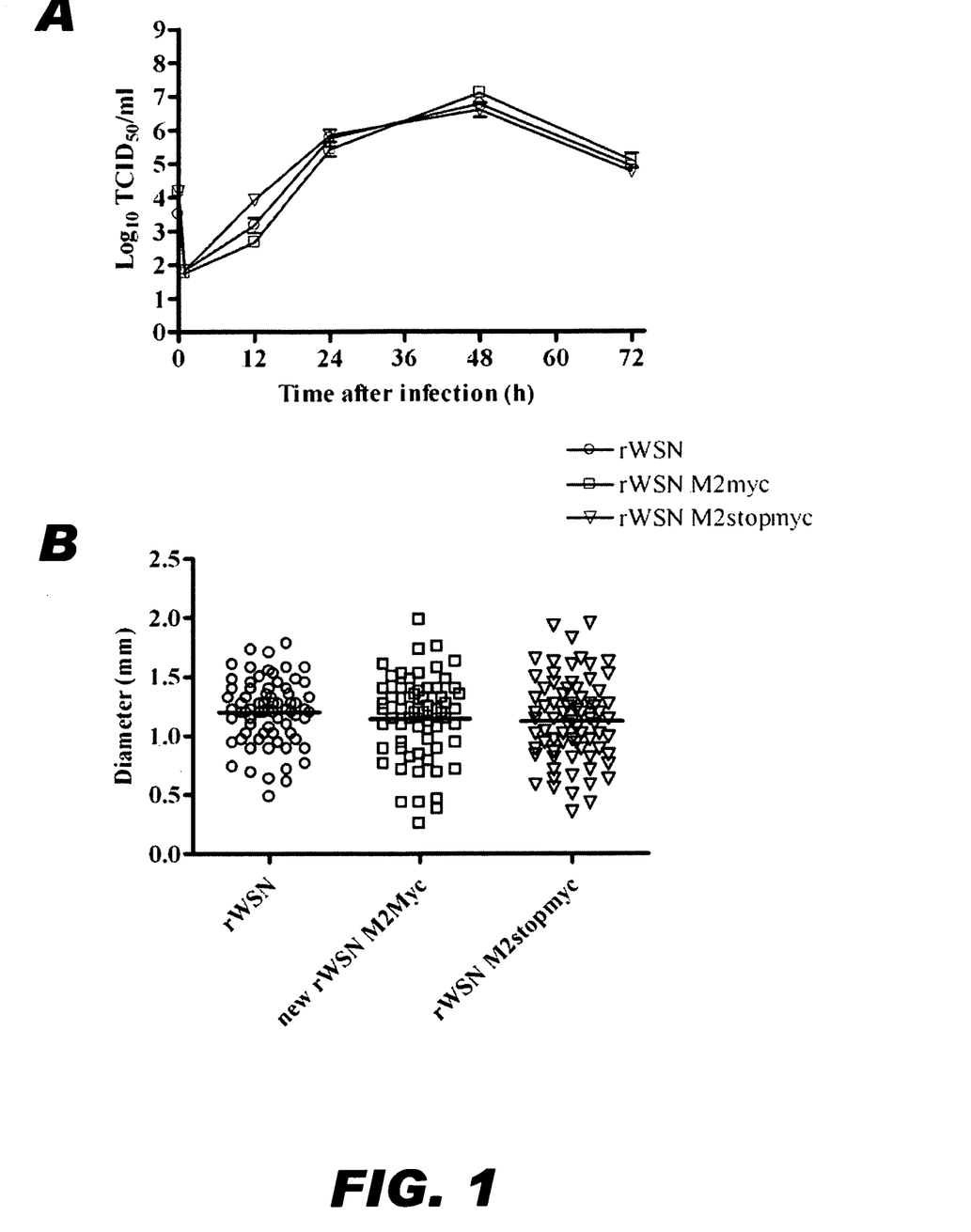

The in vitro replication of this engineered virus was indistinguishable from that of the parental rWSN virus. Madin-Darby canine kidney cells (MDCK) were infected with these viruses at low MOI (FIG. 1A) or high MOI. After a 1 hr-incubation period, the inoculum was removed and the cells were washed with media and incubated at 37° C. At particular times (i.e., 12, 24, 38, and 72 hr) after infection, the infected cell supernatant was sampled and infectious virus titers determined by $TCID_{50}$. The rWSN M2myc and the parental rWSN viruses were also analyzed by plaque assay on MDCK cells. The cells were harvested at 3 days post infection and the plaque diameter of at least 25 plaques was measured with a micrometer. The plaque morphology and diameter of the viruses was also nearly identical between the viruses (FIG. 1B), suggesting the addition of these amino acids to the M2 protein did not have an adverse effect on virus replication.

Example 2

Virulence of M2 Epitope Tagged Viruses

Figure 2:
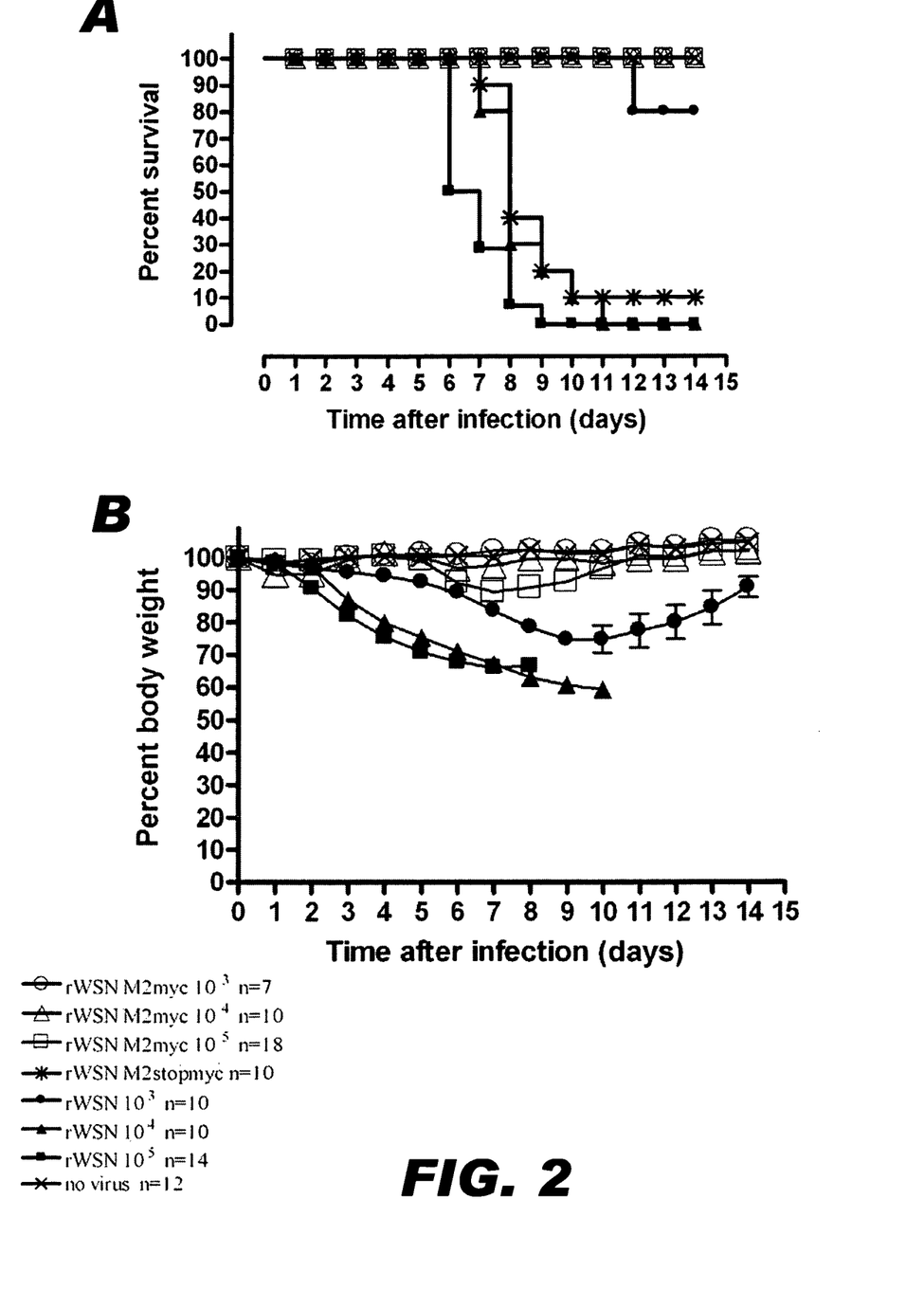

To assess the virulence of rWSN M2myc, 6-week-old Balb/c mice were anesthetized and inoculated intranasally with varying doses of rWSN M2myc or rWSN. The mice were weighed daily as a surrogate for virus-induced morbidity, and mortality was also monitored for two weeks. The rWSN M2myc virus did not induce mortality in mice while the corresponding dose of rWSN showed the expected amount of mortality (FIG. 2A). Furthermore, mice inoculated with rWSN M2myc had significantly reduced weight loss as compared to those inoculated with rWSN, indicating the recombinant virus had a drastically reduced virulence (FIG. 2B).

At day 3 and day 5 post infection, three mice from each group were sacrificed and the tracheas and lungs were removed. The viral load was determined in each organ by $TCID_{50}$. Analysis of the viral load in the tracheas (FIG. 2C) and lungs (FIG. 2D) of virus-infected mice revealed that the rWSN M2myc virus replicated to significantly lower titers than the parental rWSN virus. Taken together, these data indicate that the addition of a myc-epitope to the carboxyl terminus of M2 had little effect on virus replication in vitro, but significantly attenuated virus replication and virulence in the mouse model of infection.

Example 3

Attenuated Virulence is Due to Peptide Tag and not Additional Nucleotide Sequences In order to determine whether the addition of amino acids to the M2 cytoplasmic tail or simply the presence of additional nucleotide sequences in the engineered virus was mediating the loss of virus virulence, the authentic M2 stop codon was introduced into the M2myc coding sequence (rWSN M2stopmyc). This resulted in the production of an M2 protein that did not contain the myc epitope tag, but the viral genome did contain the nucleotide sequence for the epitope tag. This virus replicated in a manner indistinguishable from rWSN or rWSN M2 myc after low MOI infection (FIG. 1A) and with respect to plaque size and morphology (FIG. 1B), however, it regained the ability to cause mortality in mice (FIG. 2A). These data indicate that the presence of the amino acids at the carboxyl terminus of the M2 protein, but not the additional nucleotides present in the viral RNA, was responsible for attenuating virus virulence in vivo.

Example 4

M2 Epitope Tagged Viruses as Vaccines

Figure 3:
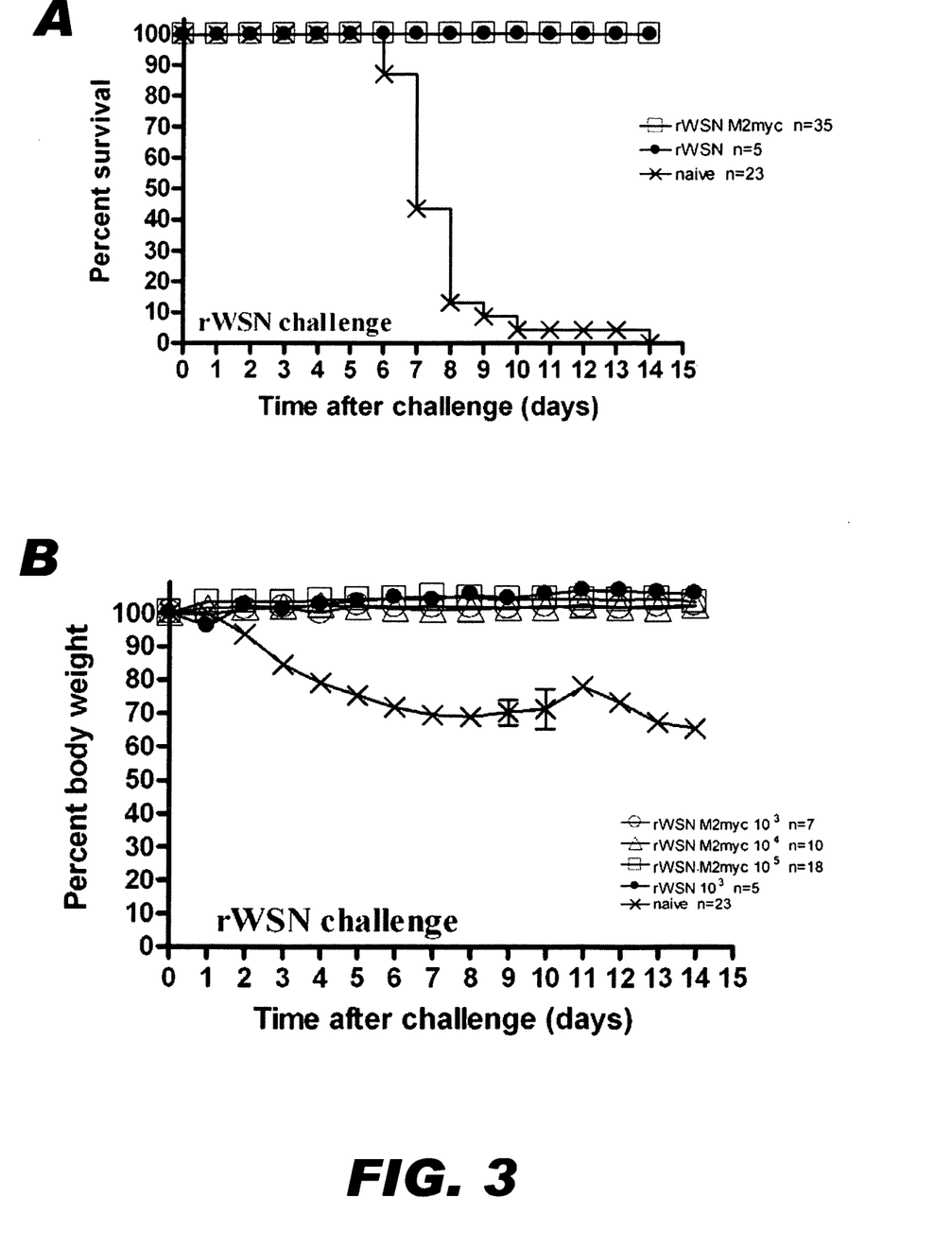
FIG. 3 illustrates that infection with rWSN M2myc protects mice from a lethal challenge with rWSN. Mice previously infected with rWSN M2myc were challenged with a lethal dose of rWSN and monitored for mortality (A) and weight loss (B). Mouse weight was normalized to the weight at the time of infection and the average and standard error are graphed. Serum was collected from mice that survived infection with either rWSN or rWSN M2myc and from immunized mice that survived a subsequent challenge with rWSN. (C) presents a plot of $TCID_{50}$ values for each condition.

Since the rWSN M2myc virus replicated but did not cause significant morbidity or mortality in infected mice, its potential as a live, attenuated influenza vaccine was assessed. Mice that had been infected with rWSN M2myc were challenged 28 days post infection with a lethal dose of rWSN (i.e., $10^6$ pfu was administered intranasally). Irrespective of the virus dose, animals that had been previously infected with rWSN M2myc survived rWSN challenge (FIG. 3A) and had very little weight loss (FIG. 3B) as compared to age-matched, naïve mice. The protection afforded by rWSN M2myc infection was equivalent to that seen in animals that were given a sublethal ($10^3$ pfu) dose of rWSN (FIGS. 3A and 3B). Although it must be noted, that the morbidity induced by sublethal rWSN infection was significantly greater than that observed with any dose of rWSN M2myc (FIG. 2B).

Figure 3C:
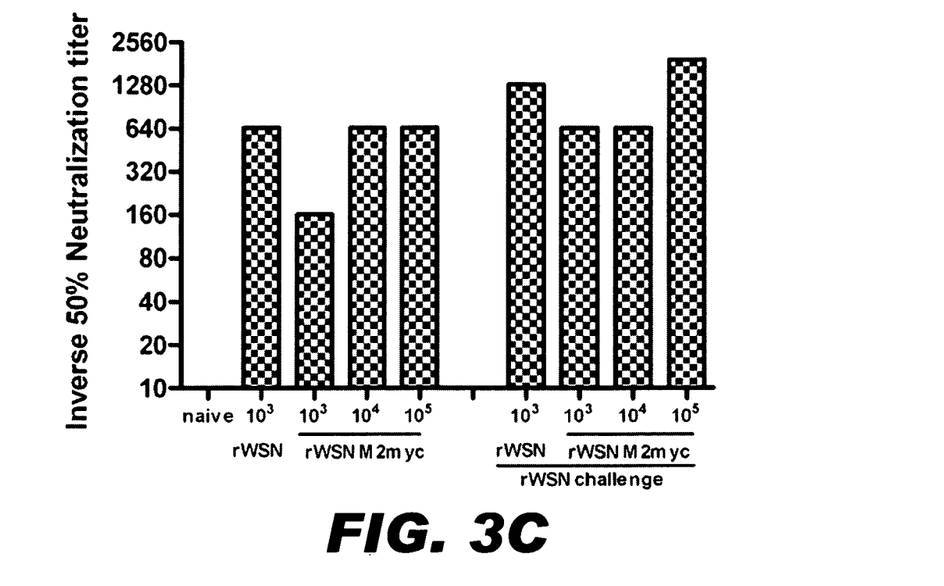
Figure 4:
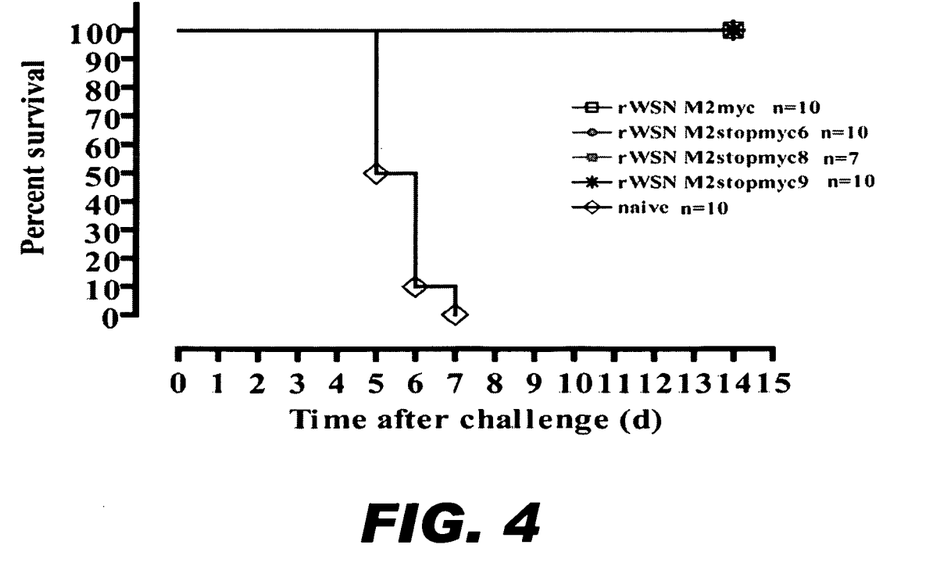
FIG. 4 illustrates a graph showing that immunization with rWSN M2myc (H1N1) viruses induces immunity to an antigenically distinct influenza virus, A/HK/68 (H3N2).

Serum was collected from mice either prior to or 28 days after rWSN challenge and the neutralizing antibody titers against rWSN determined. For this, dilutions of sera were incubated with $10^3$ pfu of rWSN, then analyzed in sextuplate by $TCID_{50}$. The serum concentration that inhibited cytopathic effect in 50% of the wells was assessed after 4 days. The level of neutralizing antibody titers in rWSN M2myc immunized mice were comparable to those in mice immunized with a sublethal rWSN (FIG. 3C). Neutralizing antibody titers rose slightly after challenge. Taken together, these data indicate that the addition of a carboxyl terminal epitope tag to the M2 protein resulted in significant attenuation of virus virulence but the immune response induced by virus infection was able to provide protection against a lethal influenza A virus challenge.

Example 5

Protection Against Challenge with Different Surface Proteins

Mice were immunized with rWSN M2 myc, or viruses containing short truncations of the myc sequence. The myc epitope is 10 amino acids long, the viruses have this sequence truncated to 9, 8 or 6 amino acids in length. These truncations maintain the attenuation of the virus. The immunized mice were then challenged with a virus that has different surface proteins from the rWSN M2myc viruses. This virus, A/HK/68 H3N2 is lethal to unimmunized mice but does not kill mice immunized with the rWSN M2myc virus, indicating that infection with the rWSN M2myc viruses has induced an immunity that protects against different influenza A virus strains. With the current influenza vaccines, separate components for H1N1 and H3N2 viruses must be included to get immunity, as these vaccines can't induce protection against antigenically unrelated viruses. The current influenza vaccines induce specific antibodies that target the H1, H3, N1 or N2 proteins and these antibodies do not recognize the other proteins. Infection with rWSN M2myc is inducing an immunity which allows for protection from antigenically unrelated viruses. This means that one vaccine virus might be able to induce protection against two different influenza A virus strains, which would be a significant improvement over current influenza vaccines.

What is claimed is:

1. An isolated influenza virus, wherein the virus comprises a M2 protein comprising a peptide tag at the carboxyl terminus, wherein
   (a) the in vitro function of the M2 protein comprising the peptide tag is not altered compared to the in vitro function of the native M2 protein,
   (b) replication of the virus in vitro is similar to that of a virulent strain of the same virus, and the replication of the virus in a host is reduced relative to that of a virulent strain of the same virus, and
   (c) the virulence of the virus in a host is reduced relative to that of a virulent strain of the same virus.

2. The isolated influenza virus of claim 1, wherein the peptide tag is from about 3 amino acids to about 30 amino acids in length.

3. The isolated influenza virus of claim 1, wherein the virus is influenza A.

4. The isolated influenza virus of claim 3, wherein the peptide tag is the myc antibody epitope tag, whose amino acid sequence consists of EQKLISEEDL (SEQ ID NO:1).

5. An immunogenic composition, wherein the composition comprises at least one live attenuated influenza virus, the virus comprising M2 protein comprising a peptide tag at the carboxyl terminus, wherein
   (a) the in vitro function of the M2 protein comprising a peptide tag is not altered compared to the in vitro function of the native M2 protein, and
   (b) replication of the virus in vitro is similar to that of a virulent strain of the same virus, and the replication of the virus in a host is reduced relative to that of a virulent strain of the same virus, and
   (c) the virulence of the virus in a host is reduced relative to that of a virulent strain of the same virus.

6. The immunogenic composition of claim 5, wherein the peptide tag is from about 3 amino acids to about 30 amino acids in length.

7. The immunogenic composition of claim 5, wherein the virus is influenza A selected from the group consisting of an H1N1 subtype, an H3N2 subtype, an H5N1 subtype, and a combination thereof.

8. The immunogenic composition of claim 7, wherein the peptide tag is the myc antibody epitope tag, whose amino acid sequence consists of EQKLISEEDL (SEQ ID NO:1).

9. The immunogenic composition of claim 7, wherein the composition further comprises an attenuated influenza B virus comprising an M2 protein comprising a peptide tag at the carboxyl terminus.

10. A method for inducing an immune response in a subject against an influenza virus, the method comprising administering to the subject an immunogenic composition comprising at least one live attenuated influenza virus, the virus comprising M2 protein comprising a peptide tag at the carboxyl terminus, wherein
    (a) the in vitro function of the M2 protein comprising the peptide tag is not altered compared to the in vitro function of the native M2 protein, and
    (b) replication of the virus in vitro is similar to that of a virulent strain of the same virus, and the replication of the virus in a host is reduced relative to that of a virulent strain of the same virus, and
    (c) the virulence of the virus in a host is reduced relative to that of a virulent strain of the same virus.

11. The method of claim 10, wherein the peptide tag is from about 3 amino acids to about 30 amino acids in length.

12. The method of claim 10, wherein the influenza virus is a type A virus selected from the group consisting of an H1N1 subtype, an H3N2 subtype, an H5N1 subtype, and a combination thereof.

13. The method of claim 12, wherein the peptide tag is the myc antibody epitope tag, whose amino acid sequence consists of EQKLISEEDL (SEQ ID NO:1).

* * * * *

SEQUENCE LISTING

<160> NUMBER OF SEQ ID NOS: 18

<210> SEQ ID NO 1
<211> LENGTH: 10
<212> TYPE: PRT
<213> ORGANISM: Artificial Sequence
<220> FEATURE:
<223> OTHER INFORMATION: ARTIFICIAL SEQUENCE TAGS

<400> SEQUENCE: 1

Glu Gln Lys Leu Ile Ser Glu Glu Asp Leu
1               5                   10

<210> SEQ ID NO 2
<211> LENGTH: 9
<212> TYPE: PRT
<213> ORGANISM: Artificial Sequence
<220> FEATURE:
<223> OTHER INFORMATION: ARTIFICIAL SEQUENCE TAGS

<400> SEQUENCE: 2

Ser Trp Lys Asp Ala Ser Gly Trp Ser
1               5

<210> SEQ ID NO 3
<211> LENGTH: 6
<212> TYPE: PRT
<213> ORGANISM: Artificial Sequence
<220> FEATURE:
<223> OTHER INFORMATION: ARTIFICIAL SEQUENCE TAGS

<400> SEQUENCE: 3

Asp Thr Tyr Arg Tyr Ile
1               5

<210> SEQ ID NO 4
<211> LENGTH: 6
<212> TYPE: PRT
<213> ORGANISM: Artificial Sequence
<220> FEATURE:
<223> OTHER INFORMATION: ARTIFICIAL SEQUENCE TAGS

<400> SEQUENCE: 4

Thr Asp Phe Tyr Leu Lys
1               5

<210> SEQ ID NO 5
<211> LENGTH: 13
<212> TYPE: PRT
<213> ORGANISM: Artificial Sequence
<220> FEATURE:
<223> OTHER INFORMATION: ARTIFICIAL SEQUENCE TAGS

<400> SEQUENCE: 5

Gly Ala Pro Val Pro Tyr Pro Asp Pro Leu Glu Pro Arg
1               5                   10

<210> SEQ ID NO 6
<211> LENGTH: 5
<212> TYPE: PRT
<213> ORGANISM: Artificial Sequence
<220> FEATURE:
<223> OTHER INFORMATION: ARTIFICIAL SEQUENCE TAGS

<400> SEQUENCE: 6

Asp Asp Asp Asp Lys
1               5

```
<210> SEQ ID NO 7
<211> LENGTH: 10
<212> TYPE: PRT
<213> ORGANISM: Artificial Sequence
<220> FEATURE:
<223> OTHER INFORMATION: ARTIFICIAL SEQUENCE TAGS

<400> SEQUENCE: 7

Ser Ser Thr Ser Ser Asp Phe Arg Asp Arg
1               5                   10

<210> SEQ ID NO 8
<211> LENGTH: 8
<212> TYPE: PRT
<213> ORGANISM: Artificial Sequence
<220> FEATURE:
<223> OTHER INFORMATION: ARTIFICIAL SEQUENCE TAGS

<400> SEQUENCE: 8

Asp Tyr Lys Asp Asp Asp Asp Lys
1               5

<210> SEQ ID NO 9
<211> LENGTH: 6
<212> TYPE: PRT
<213> ORGANISM: Artificial Sequence
<220> FEATURE:
<223> OTHER INFORMATION: ARTIFICIAL SEQUENCE TAGS

<400> SEQUENCE: 9

Glu Tyr Met Pro Met Glu
1               5

<210> SEQ ID NO 10
<211> LENGTH: 12
<212> TYPE: PRT
<213> ORGANISM: Artificial Sequence
<220> FEATURE:
<223> OTHER INFORMATION: ARTIFICIAL SEQUENCE TAGS

<400> SEQUENCE: 10

Gln Pro Glu Leu Ala Pro Glu Asp Pro Glu Asp Cys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: ARTIFICIAL SEQUENCE TAGS

<400> SEQUENCE: 11

Lys Pro Pro Thr Pro Pro Pro Glu Pro Glu Thr
1               5                   10

<210> SEQ ID NO 12
<211> LENGTH: 15
<212> TYPE: PRT
<213> ORGANISM: Artificial Sequence
<220> FEATURE:
<223> OTHER INFORMATION: ARTIFICIAL SEQUENCE TAGS

<400> SEQUENCE: 12

Lys Glu Thr Ala Ala Ala Lys Phe Glu Arg Gln His Met Asp Ser
1               5                   10                  15
```

```
<210> SEQ ID NO 13
<211> LENGTH: 9
<212> TYPE: PRT
<213> ORGANISM: Artificial Sequence
<220> FEATURE:
<223> OTHER INFORMATION: ARTIFICIAL SEQUENCE TAGS

<400> SEQUENCE: 13

Asn Ala Asn Asn Pro Asp Trp Asp Phe
1               5

<210> SEQ ID NO 14
<211> LENGTH: 11
<212> TYPE: PRT
<213> ORGANISM: Artificial Sequence
<220> FEATURE:
<223> OTHER INFORMATION: ARTIFICIAL SEQUENCE TAGS

<400> SEQUENCE: 14

Met Ala Ser Met Thr Gly Gly Gln Gln Met Gly
1               5                   10

<210> SEQ ID NO 15
<211> LENGTH: 14
<212> TYPE: PRT
<213> ORGANISM: Artificial Sequence
<220> FEATURE:
<223> OTHER INFORMATION: ARTIFICIAL SEQUENCE TAGS

<400> SEQUENCE: 15

Gly Lys Pro Ile Pro Asn Pro Leu Leu Gly Leu Asp Ser Thr
1               5                   10

<210> SEQ ID NO 16
<211> LENGTH: 11
<212> TYPE: PRT
<213> ORGANISM: Artificial Sequence
<220> FEATURE:
<223> OTHER INFORMATION: ARTIFICIAL SEQUENCE TAGS

<400> SEQUENCE: 16

Tyr Thr Asp Ile Glu Met Asn Arg Leu Gly Lys
1               5                   10

<210> SEQ ID NO 17
<211> LENGTH: 6
<212> TYPE: PRT
<213> ORGANISM: Artificial Sequence
<220> FEATURE:
<223> OTHER INFORMATION: ARTIFICIAL SEQUENCE TAGS

<400> SEQUENCE: 17

His His His His His His
1               5

<210> SEQ ID NO 18
<211> LENGTH: 30
<212> TYPE: DNA
<213> ORGANISM: Influenza virus

<400> SEQUENCE: 18
gagcagaagc tgatctccga ggaagacctg                              30
```